(12) United States Patent
Wei

(10) Patent No.: US 10,085,924 B2
(45) Date of Patent: Oct. 2, 2018

(54) PERSONAL CARE COMPOSITIONS

(71) Applicant: The Procter & Gamble Company, Cincinnati, OH (US)

(72) Inventor: Karl Shiqing Wei, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/937,089

(22) Filed: Nov. 10, 2015

(65) Prior Publication Data
US 2016/0128917 A1    May 12, 2016

Related U.S. Application Data

(60) Provisional application No. 62/077,899, filed on Nov. 10, 2014.

(51) Int. Cl.
| | | |
|---|---|---|
| *A61K 8/11* | (2006.01) | |
| *A61Q 19/10* | (2006.01) | |
| *A61K 8/37* | (2006.01) | |
| *A61K 8/46* | (2006.01) | |
| *A61K 8/41* | (2006.01) | |
| *A61Q 13/00* | (2006.01) | |
| *A61K 8/92* | (2006.01) | |

(52) U.S. Cl.
CPC ............ *A61K 8/11* (2013.01); *A61K 8/375* (2013.01); *A61K 8/416* (2013.01); *A61K 8/46* (2013.01); *A61K 8/463* (2013.01); *A61K 8/922* (2013.01); *A61Q 13/00* (2013.01); *A61Q 19/10* (2013.01); *A61K 2800/412* (2013.01); *A61K 2800/596* (2013.01); *A61K 2800/624* (2013.01)

(58) Field of Classification Search
None
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer et al. | |
| 2,658,072 A | 11/1953 | Kosmin | |
| 3,915,921 A | 10/1975 | Schlatzer, Jr. | |
| 3,940,351 A | 2/1976 | Schlatzer, Jr. | |
| 4,062,817 A | 12/1977 | Westerman | |
| 4,429,097 A | 1/1984 | Chang et al. | |
| 5,011,681 A | 4/1991 | Ciotti et al. | |
| 5,147,576 A | 9/1992 | Montague et al. | |
| 5,364,617 A | 11/1994 | Bush et al. | |

(Continued)

FOREIGN PATENT DOCUMENTS

| | | |
|---|---|---|
| DE | 10 2008 035 172 A1 | 2/2010 |
| EP | 1 383 542 B1 | 4/2008 |

(Continued)

OTHER PUBLICATIONS

International Search Report PCT/US2015/059926 including the Written Opinion of the International Searching Authority, dated Jan. 8, 2016, 12 pages.

(Continued)

*Primary Examiner* — Necholus Ogden, Jr.

(57) ABSTRACT

A personal care composition includes a structured cleansing phase; a benefit phase including triglycerides, a cationic deposition polymer, and anionic microcapsules; and a carrier; and methods relating thereto.

18 Claims, 6 Drawing Sheets

(56) References Cited

U.S. PATENT DOCUMENTS

| | | | |
|---|---|---|---|
| 5,462,963 A | 10/1995 | Bush et al. | |
| 5,487,884 A | 1/1996 | Bissett et al. | |
| 5,652,228 A | 7/1997 | Bissett | |
| 5,681,852 A | 10/1997 | Bissett | |
| 5,965,502 A | 10/1999 | Balzer | |
| 6,068,834 A | 5/2000 | Kvalnes et al. | |
| 6,150,312 A | 11/2000 | Puvvada et al. | |
| 6,217,888 B1 | 4/2001 | Oblong et al. | |
| 6,395,691 B1 | 5/2002 | Tsaur | |
| 6,433,061 B1 | 8/2002 | Marchant et al. | |
| 6,537,527 B1 | 3/2003 | Kvalnes et al. | |
| 6,635,702 B1 | 10/2003 | Schmucker-Castner et al. | |
| 6,645,511 B2 | 11/2003 | Aronson et al. | |
| 6,759,376 B2 | 7/2004 | Zhang et al. | |
| 6,780,826 B2 | 8/2004 | Zhang et al. | |
| 6,849,584 B2* | 2/2005 | Geary | A61K 8/0295 510/119 |
| 6,897,253 B2 | 5/2005 | Schmucker-Castner et al. | |
| 7,084,104 B2 | 8/2006 | Martin et al. | |
| 7,098,180 B2 | 8/2006 | Ganopolsky et al. | |
| 7,119,059 B2 | 10/2006 | Librizzi et al. | |
| 7,157,414 B2 | 1/2007 | Librizzi et al. | |
| 7,488,707 B2 | 2/2009 | Frantz et al. | |
| 7,511,003 B2 | 3/2009 | Focht et al. | |
| 7,527,077 B2 | 5/2009 | McCall et al. | |
| 7,531,497 B2 | 5/2009 | Midha et al. | |
| 7,649,047 B2 | 1/2010 | Tamareselvy et al. | |
| 7,666,825 B2 | 2/2010 | Wagner et al. | |
| 7,754,666 B2 | 7/2010 | Walters et al. | |
| 7,763,419 B2 | 7/2010 | Hendrix et al. | |
| 7,767,389 B2 | 8/2010 | Hendrix et al. | |
| 7,771,924 B2 | 8/2010 | Hendrix et al. | |
| 7,771,925 B2 | 8/2010 | Hendrix et al. | |
| 8,067,517 B2 | 11/2011 | Yoshinaka et al. | |
| 8,105,996 B2 | 1/2012 | Wei et al. | |
| 8,309,667 B2 | 11/2012 | Yoshinaka et al. | |
| 2002/0042448 A1* | 4/2002 | Sorrentino | A61K 8/19 514/772.4 |
| 2004/0092415 A1 | 5/2004 | Focht et al. | |
| 2004/0223929 A1 | 11/2004 | Clapp et al. | |
| 2004/0223991 A1 | 11/2004 | Wei et al. | |
| 2004/0235702 A1 | 11/2004 | Hawkins | |
| 2005/0019299 A1 | 1/2005 | Librizzi et al. | |
| 2005/0020468 A1 | 1/2005 | Rhodia | |
| 2005/0049172 A1 | 3/2005 | Lukenbach et al. | |
| 2005/0075256 A1 | 4/2005 | Librizzi et al. | |
| 2005/0100570 A1 | 5/2005 | Wei et al. | |
| 2005/0276768 A1 | 12/2005 | Wei et al. | |
| 2006/0040834 A1 | 2/2006 | Hilliard et al. | |
| 2006/0079419 A1 | 4/2006 | Wagner et al. | |
| 2006/0079420 A1 | 4/2006 | Wagner et al. | |
| 2006/0079421 A1 | 4/2006 | Wagner et al. | |
| 2006/0182699 A1 | 8/2006 | Taylor et al. | |
| 2006/0189495 A1 | 8/2006 | Librizzi et al. | |
| 2007/0155637 A1 | 7/2007 | Smith et al. | |
| 2007/0196344 A1 | 8/2007 | Osborne et al. | |
| 2007/0224696 A1 | 9/2007 | Honkonen et al. | |
| 2007/0286832 A1 | 12/2007 | Clapp et al. | |
| 2008/0095733 A1 | 4/2008 | Griffin et al. | |
| 2008/0112913 A1 | 5/2008 | Librizzi et al. | |
| 2008/0233061 A1 | 9/2008 | Gates et al. | |
| 2008/0242573 A1 | 10/2008 | Wei | |
| 2009/0005449 A1 | 1/2009 | Gunn et al. | |
| 2009/0005460 A1 | 1/2009 | Gunn et al. | |
| 2009/0311348 A1 | 12/2009 | Einarsson et al. | |
| 2010/0028376 A1 | 2/2010 | Einarsson et al. | |
| 2010/0158830 A1 | 6/2010 | Wei et al. | |
| 2010/0216707 A1 | 8/2010 | Bernard et al. | |
| 2010/0322878 A1 | 12/2010 | Stella et al. | |
| 2011/0038830 A1 | 2/2011 | Bernard et al. | |
| 2011/0091439 A1 | 4/2011 | Bernard et al. | |
| 2011/0257020 A1 | 10/2011 | Stella et al. | |
| 2011/0257030 A1 | 10/2011 | Stella et al. | |
| 2011/0268802 A1 | 11/2011 | Dihora et al. | |
| 2011/0269657 A1 | 11/2011 | Dihora et al. | |
| 2011/0280822 A1 | 11/2011 | Griffin et al. | |
| 2012/0009285 A1 | 1/2012 | Wei et al. | |
| 2012/0184448 A1 | 7/2012 | Stella et al. | |
| 2012/0276175 A1 | 11/2012 | Dihora et al. | |
| 2012/0276177 A1* | 11/2012 | Hilliard, Jr. | A61K 8/0245 424/401 |
| 2012/0276210 A1 | 11/2012 | Dihora et al. | |
| 2012/0282309 A1 | 11/2012 | Dihora et al. | |
| 2012/0316095 A1 | 12/2012 | Wei et al. | |
| 2013/0149273 A1 | 6/2013 | Wei et al. | |
| 2013/0225468 A1 | 8/2013 | Corominas et al. | |
| 2013/0253057 A1 | 9/2013 | Wei et al. | |
| 2013/0280356 A1 | 10/2013 | Stella et al. | |
| 2013/0281551 A1 | 10/2013 | Stella et al. | |
| 2016/0128913 A1 | 5/2016 | Wei et al. | |
| 2016/0128927 A1 | 5/2016 | Wei et al. | |
| 2016/0128930 A1 | 5/2016 | Stella et al. | |

FOREIGN PATENT DOCUMENTS

| | | |
|---|---|---|
| FR | 2 924 947 B1 | 3/2010 |
| FR | 2 925 314 A | 11/2012 |
| FR | 2 908 784 B1 | 12/2012 |
| FR | 2 924 613 B1 | 12/2012 |
| FR | 2 924 614 B1 | 12/2012 |
| GB | 2245585 A | 8/1992 |
| JP | S 61155311 A | 7/1986 |
| JP | 03095110 A2 | 4/1991 |
| JP | 04149112 A | 5/1992 |
| JP | 2009084224 A | 4/2009 |
| WO | WO 95/34280 A1 | 12/1995 |
| WO | WO 2009/081368 A2 | 7/2009 |
| WO | WO 2010/079468 A2 | 7/2010 |
| WO | WO 2012/138710 A2 | 10/2012 |

OTHER PUBLICATIONS

U.S. Appl. No. 61/657,145, filed Jun. 8, 2012, Karl Shiqing Wei et al.

U.S. Appl. No. 61/442,651, filed Jan. 5, 2017, Karl Shiqing Wei.

* cited by examiner

PERSONAL CARE COMPOSITIONS

TECHNICAL FIELD

The present disclosure relates to personal care compositions that include microcapsules and triglycerides; and methods relating thereto.

BACKGROUND

Cleansing the skin is an activity that has been done for millennia. Skin cleansing and methods therefore have involved the utilization of soaps, body washes, and other personal care compositions. Personal care compositions can be structured to suspend and stabilize dispersions of benefit agents while maintaining physical integrity of the compositions, and there are many ways to provide such structure. The ability to provide structure can be an important property for such compositions, but it is also important for personal care compositions to have the ability to rapidly become micellar upon dilution to clean the skin and to deposit benefit agents. Having too much structure in a composition can result in poor performance, but not having enough structure in a composition can cause the product to be unstable. Further, achieving a balance between these two properties can be a difficult task. Furthermore, such personal care compositions also often include fragrances. Such fragrances may delight the user by providing a freshness feeling and may serve as a signal to the user that the product may still be working or that the product is still present. Yet because of the volatility of many fragrances and/or habituation, a consumer may be unable to notice the fragrance shortly after using/applying the personal care composition. Consequentially, it may be desirable to have technologies than improve the noticeability of fragrances in personal care compositions while also providing structure to the personal care composition.

SUMMARY

A personal care composition comprising a structured cleansing phase comprising about 2% to about 50% of an anionic surfactant and a benefit phase comprising triglycerides; from about 0.01% to about 2% of a cationic deposition polymer; a plurality of anionic microcapsules; and a carrier.

A method of making a personal care composition, the method comprising adding a premix, said premix comprising a plurality of anionic microcapsules and a cationic deposition polymer to a mixture comprising a structured cleansing phase comprising about 2% to about 50% of an anionic surfactant, a benefit phase comprising triglycerides, and a carrier to form a personal care composition.

BRIEF DESCRIPTION OF THE DRAWINGS

While the specification concludes with claims, it is believed that the same will be better understood from the following description taken in conjunction with the accompanying drawings in which:

DETAILED DESCRIPTION

Figure 1:
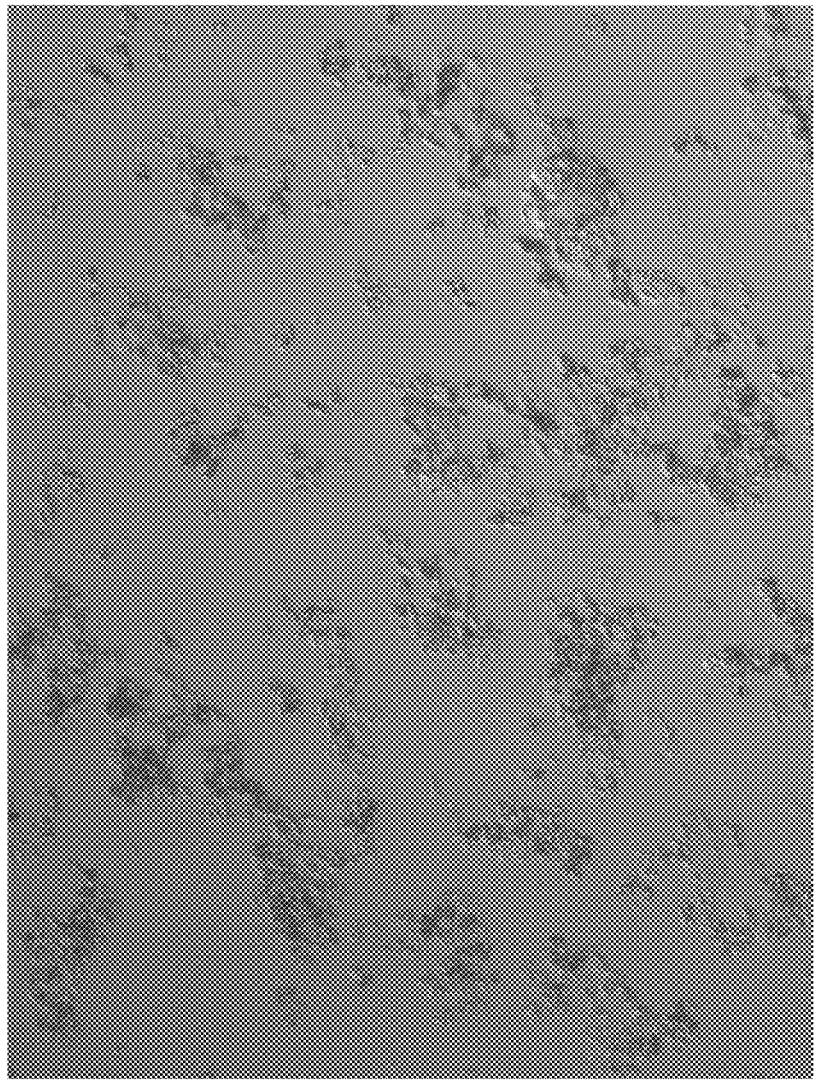
FIG. 1 is an image showing a dilution of 1 part of a personal care composition including 7% by weight of the composition of soybean oil to 9 parts of water.
Figure 2:
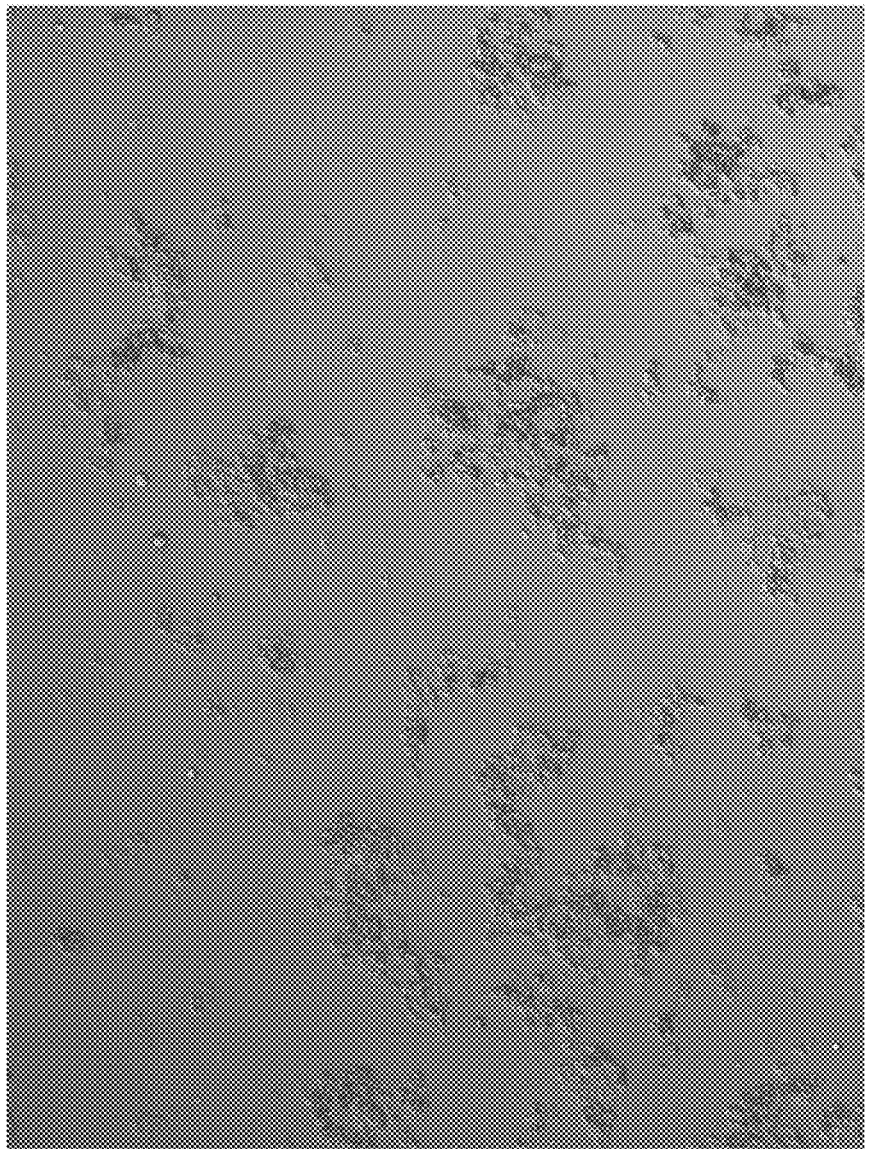
FIG. 2 is an image showing a dilution of 1 part of a personal care composition including 7% by weight of the composition of soybean oil and 0.2% by weight of the composition of anionic microcapsules with a cationic deposition polymer without premixing the microcapsules and polymer (having a core material including a perfume oil and a polyacrylate wall material) to 9 parts of water that results in a lack of clusters of microcapsules.
Figure 3:
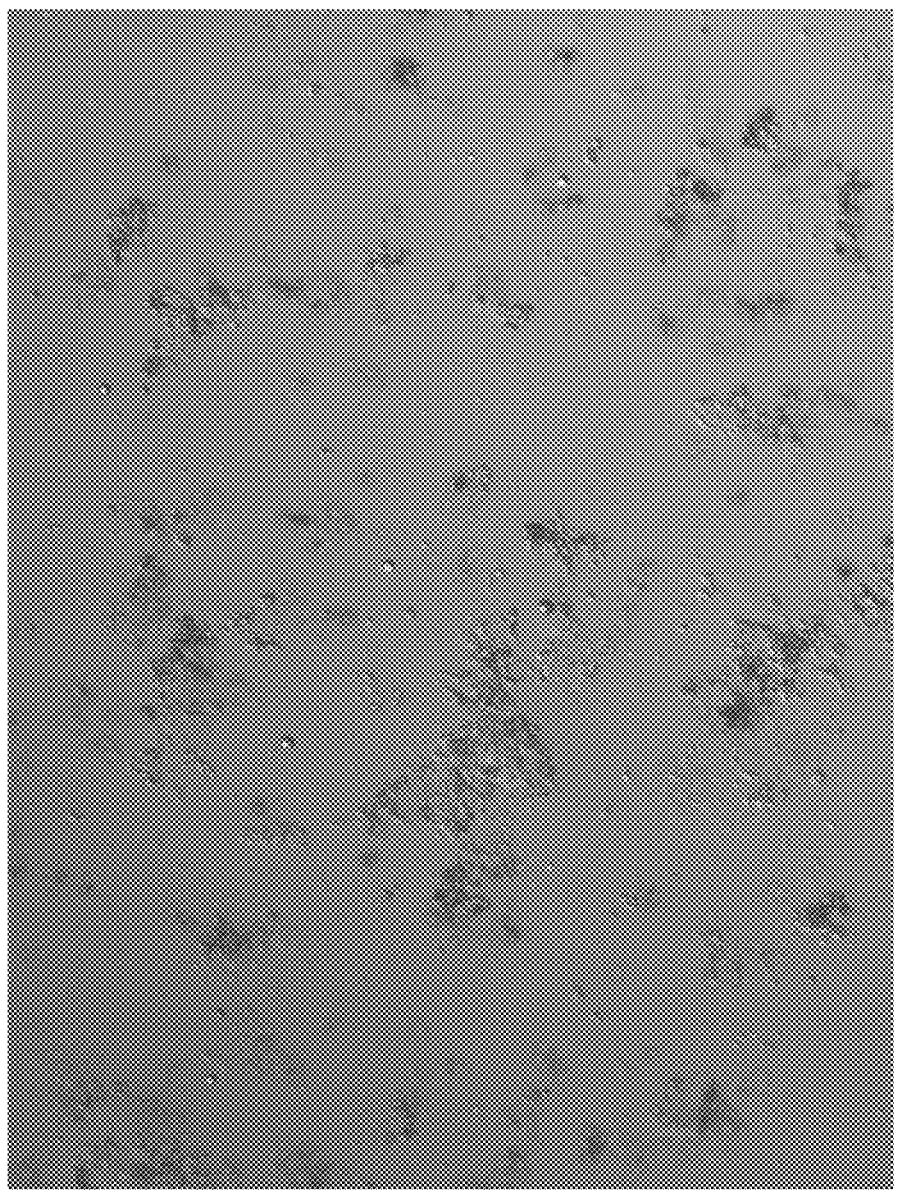
FIG. 3 is an image showing a dilution of 1 part of a personal care composition including 7% by weight of the composition of soybean oil and 0.2% by weight of the composition of non-ionic microcapsules (having a core material including a perfume oil and a polyacrylate wall material) to 9 parts of water that results in a lack of clusters of microcapsules.
Figure 4:
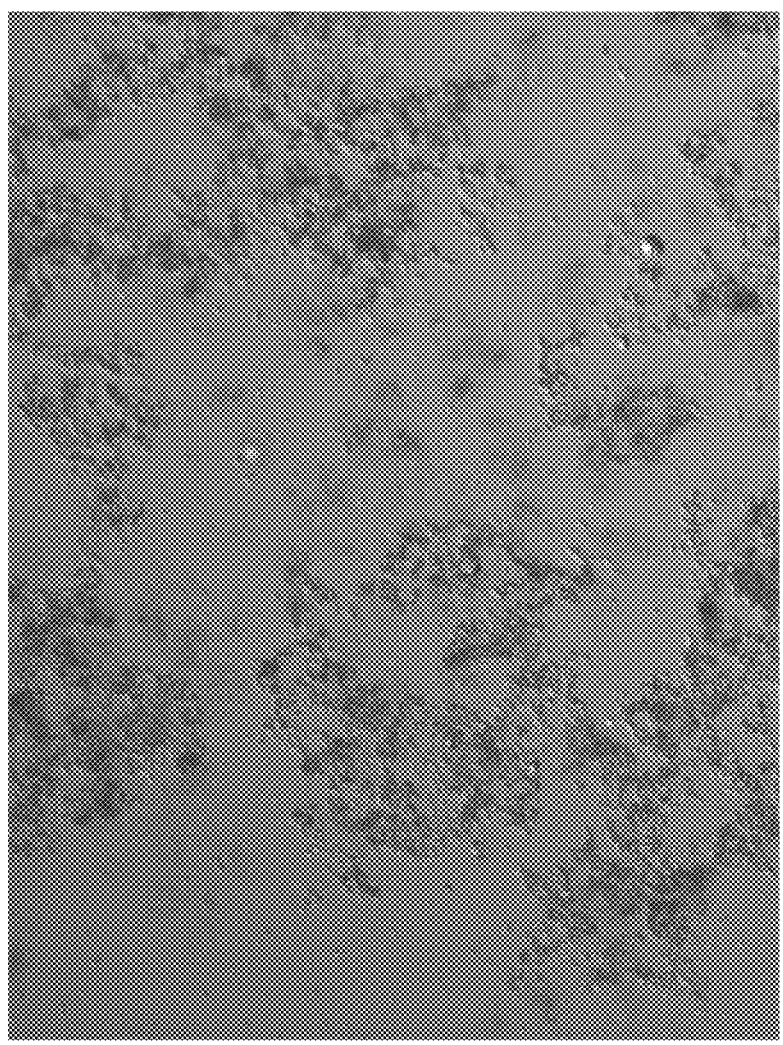
FIG. 4 is an image showing a dilution of 1 part of a personal care composition including 7% by weight of the composition of soybean oil and 0.2% by weight of the composition of cationic microcapsules (having a core material including a perfume oil and a polyacrylate wall material) to 9 parts of water that results in a lack of clusters of microcapsules.
Figure 5:
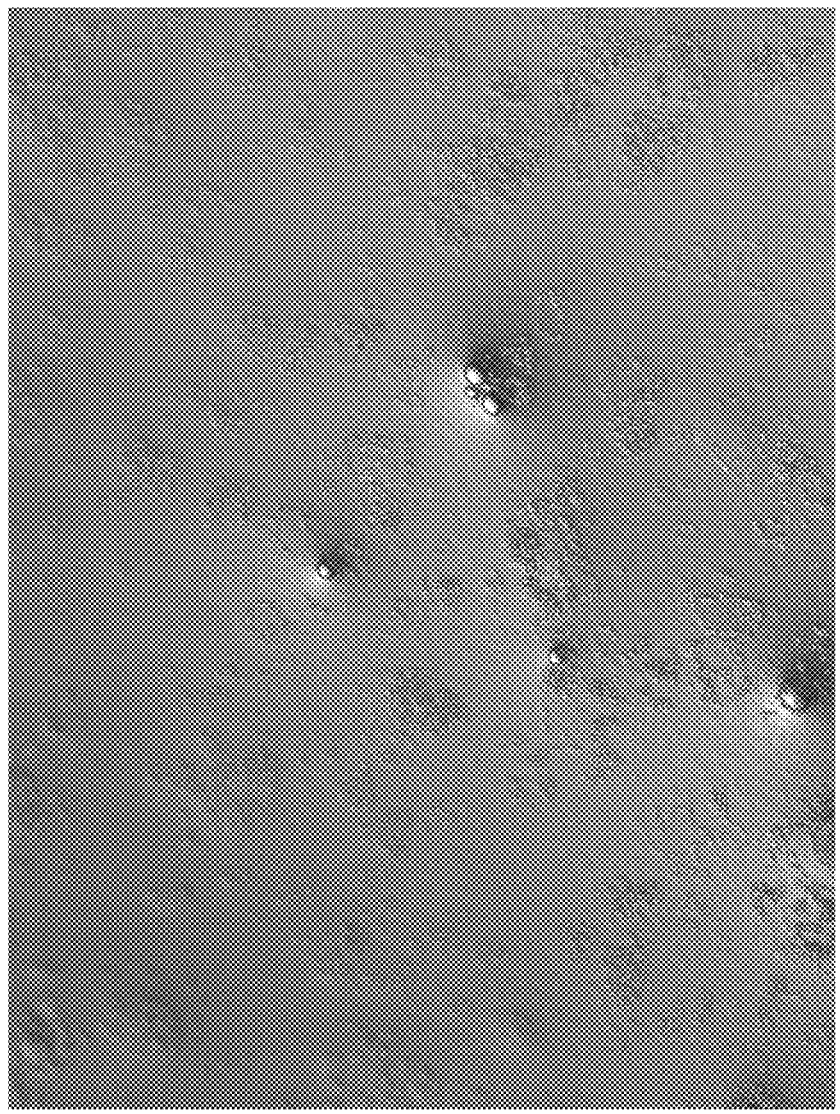
FIG. 5 is an image showing a dilution of 1 part of a personal care composition including 7% by weight of the composition of soybean oil and 0.2% by weight of the composition of anionic microcapsules (having a core material including a perfume oil and a wall material made from melamine-formaldehyde condensates) to 9 parts of water that results in the formation clusters of microcapsules, where the microcapsules and cationic polymer are formed into a premix.
Figure 6:
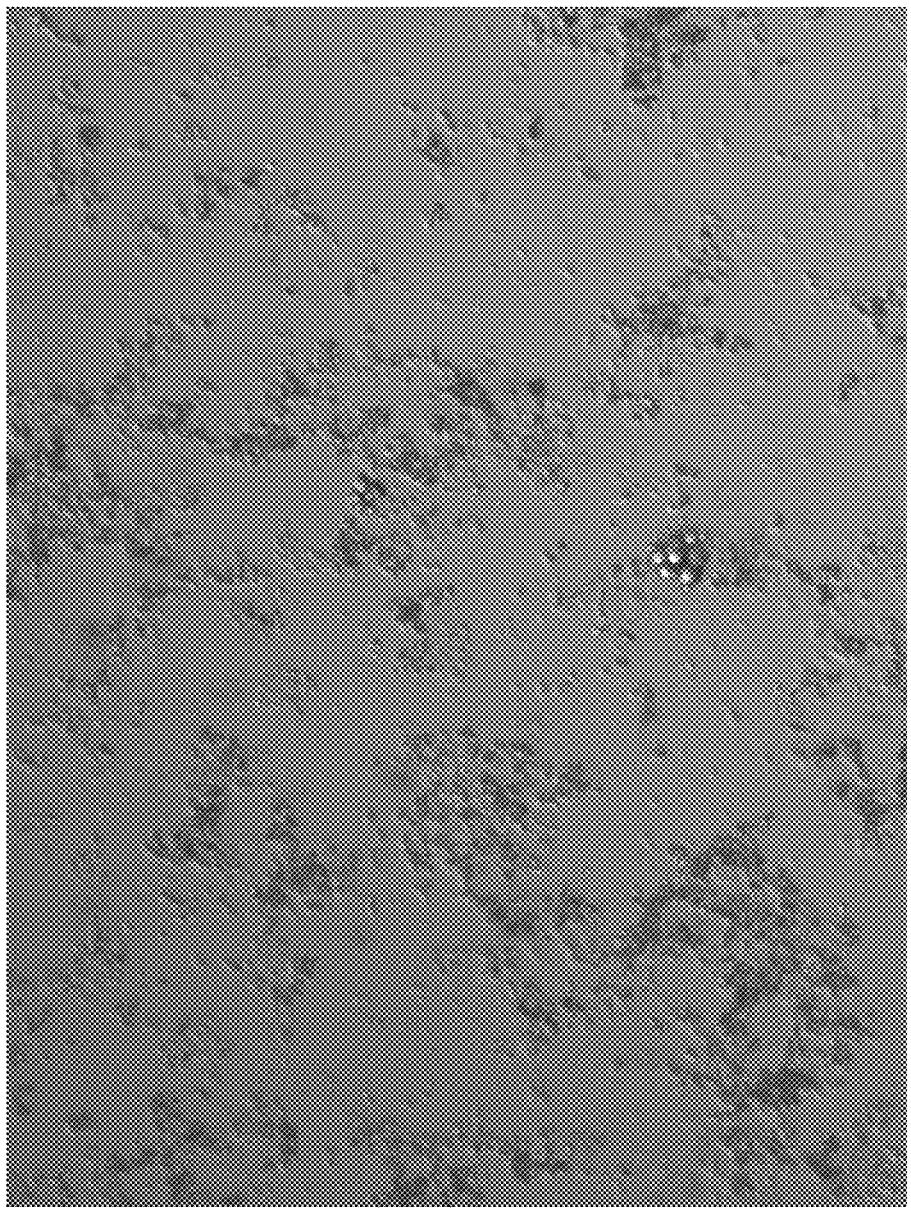
FIG. 6 is an image showing a dilution of 1 part of a personal care composition including 7% by weight of the composition of soybean oil and 0.2% by weight of the composition of anionic microcapsules (having a core material including a perfume oil that is different from the microcapsules used in FIG. 5 and a wall material made from melamine-formaldehyde condensates) to 9 parts of water that results in the formation of clusters of microcapsules, where the microcapsules and cationic polymer are formed into a premix.

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated.

All measurements used herein are in metric units unless otherwise specified.

I. Definitions

As used herein, the following terms shall have the meaning specified thereafter:

"Anhydrous" refers to those compositions, and components thereof, which are substantially free of water.

"Anionic microcapsules" refer to microcapsules with a zeta potential of less than negative 0.5 millivolts as determined by the method described herein.

"Associative polymer" refers to a water-dispersible polymer comprising hydrophobic groups at an end or pendants to a hydrophilic backbone.

"Molecular weight" as used herein with respect to polymers refers to the weight average molecular weight unless otherwise specified.

"Multiphase" refers to compositions comprising at least two phases which can be chemically distinct (e.g., a structured cleansing phase and a benefit phase). Such phases can be in direct physical contact with one another. A personal care composition can be a multiphase personal care composition where phases of the personal care composition can be blended or mixed to a significant degree, but still be physically distinct. In these situations, the physical distinctiveness is undetectable to the naked eye. The personal care composition can also be a multiphase personal care composition where phases of the personal care composition can be made to occupy separate but distinct physical spaces inside a package in which the phases can be stored. In such an arrangement, the phases can be stored such that they are not in direct contact with one another (i.e., the phases are not separated by a barrier and the phases are not emulsified or mixed to any significant degree). The personal care composition can also be a multiphase personal care composition where the phases are in physical contact and are visually distinct. Visually distinct phases can take many forms (e.g., phases can appear as striped, marbled). The personal care composition can also include a combination of one or more of the above multiphase personal care compositions. In one such an arrangement, one blended multiphase personal care composition can be stacked with another blended multiphase personal care composition to form a striped configuration. Additionally, blended multiphase personal care compositions distinguishable by color can be stacked as stripes wherein the blended multiphase personal care compositions can be otherwise similar in average composition.

"Non-associative polymer" refers to a water-dispersible polymer with a relatively uniform hydrophilic backbone lacking hydrophobic groups.

"Package" refers to any suitable container for a personal care composition including but not limited to a bottle, tottle, tube, jar, non-aerosol pump, and combinations thereof.

"Personal care composition" refers to compositions intended for topical application to skin or hair. Personal care compositions can be rinse-off formulations, in which the product can be applied topically to the skin or hair and then subsequently rinsed within seconds to minutes from the skin or hair with water. The product could also be wiped off using a substrate. In either case, it is believed at least a portion of the product is left behind (i.e., deposited) on the skin. The personal care compositions can also be used as shaving aids. The personal care compositions can be extrudable or dispensable from a package. The personal care compositions can exhibit a viscosity of from about 1,500 cP to about 1,000,000 cP as measured by a viscosity method as described in the commonly owned, patent application published on Nov. 11, 2004 under U.S. Publication No. 2004/0223991 A1 entitled, "Multiphase Personal Care Compositions" filed on May 7, 2004 by Wei, et al. The personal care compositions can be in the form of, for example, a liquid, semi-liquid cream, lotion, or gel and are intended for topical application to the skin and/or hair. Examples of personal care compositions can include but are not limited to bar soap, shampoo, conditioning shampoo, body wash, moisturizing body wash, shower gels, skin cleansers, cleansing milks, hair and body wash, in shower body moisturizer, pet shampoo, shaving preparations, and cleansing compositions used in conjunction with a disposable cleansing cloth.

The term "premix" when used with respect to microcapsules refers to a mixture that is formed by combining a plurality of anionic microcapsules with a cationic deposition polymer.

"STnS" refers to sodium trideceth(n) sulfate, wherein n can define the average number of moles of ethoxylate per molecule.

"Stable" refers to a personal care composition having a viscosity change of about 30% or less from an initial viscosity value after being rapidly aged for 10 days at 50° C.

"Structured" refers to having a rheology that can confer stability on the personal care composition. A degree of structure can be determined by characteristics determined by a Zero Shear Viscosity Method described below. Accordingly, a structured cleansing phase of the personal care composition can be considered to be structured if the structured cleansing phase has a Zero Shear Viscosity of about 20 Pascal-seconds (Pa-s) or more, about 200 Pa-s or more, about 500 Pa-s or more, about 1,000 Pa-s or more, about 1,500 Pa-s or more, or about 2,000 Pa-s or more. Other methods for determining characteristics which can define a degree of structure are described in U.S. Patent Application Publication No. 2012/0009285.

The phrase "substantially free of" as used herein, unless otherwise specified means that the personal care composition comprises less than about 5%, less than about 3%, less than about 1%, or even less than about 0.1% of the stated ingredient. The term "free of" as used herein means that the personal care composition comprises 0% of the stated ingredient that is the ingredient has not been added to the personal care composition. However, these ingredients may incidentally form as a by-product or a reaction product of the other components of the personal care composition.

"Surfactant component" refers to a total of all anionic, nonionic, amphoteric, zwitterionic, and cationic surfactants in a phase. When calculations are based on the surfactant component, water and electrolytes can be excluded from the calculations involving the surfactant component since surfactants as manufactured can be diluted and neutralized.

"Visually distinct" generally refers to a region of the multiphase personal care composition having one average composition, as distinct from another region having a different average composition, wherein the regions can be visible to the unaided naked eye. This would not preclude distinct regions from comprising two similar multiphase personal care compositions or phases where one multiphase personal care composition or phase can comprise certain pigments, dyes, particles, and various optional ingredients, hence providing a region of different average composition (e.g., different textures or different colors).

II. Personal Care Compositions

It has been surprisingly found that the development of clusters of microcapsules is important for the deposition of microcapsules delivered to a situs via a personal cleansing composition. In this regard, the formation of clusters of microcapsules upon dilution of the personal cleansing composition containing microcapsules may improve the deposition of the microcapsules, and thereby lead to a more noticeable bloom from the microcapsules. It has been found that the formation of clusters of microcapsules may be initiated by combining anionic microcapsules (microcapsules with a zeta potential of less than negative 0.5 millivolts) with a cationic deposition polymer to form a premix. It has also surprisingly been found that the choice of benefit agent may influence the development of clusters. In this regard, it has been surprisingly found that the presence of a benefit agent comprising triglycerides may also increase the development of clusters, and thereby leading to an improvement in the performance of the microcapsules A. Structured Cleansing Phase As noted herein, a personal care composition can include a structured cleansing phase and a benefit phase. The structured cleansing phase and the benefit phase can be in physical contact. The phases can be blended or mixed to a significant degree, but still be physically distinct such that the physical distinctiveness is undetectable to the naked eye. The phases can also be made to occupy separate but distinct physical spaces inside a package in which the phases are stored. In such an arrangement, the structured cleansing phase and the benefit phase can be stored such that the phases are not in direct contact with one another. The phases can also be in physical contact where the phases are visibly distinct which, for example, can give a striped or marbled configuration.

The personal care composition can include a combination of one or more of the above multiphase personal care compositions. For example, one blended multiphase personal care composition can be stacked as stripes with another blended multiphase personal care composition.

The personal care composition of the present invention includes a cleansing phase. The cleansing phase will comprise as least one anionic surfactant. The surfactant may be present from about 3% to about 20%, by weight of the personal care composition. The cleansing phase may contain from 3% to about 20%, from about 5% to about 15%, from about from about 7% to about 15%, from about 5% to about 13%, or any combination of the upper, lower, and included limits within the ranges.

The cleansing phase may be structured. When structured, the cleansing phase is comprised of a structured domain. The structured domain is preferably an opaque structured domain, which is preferably a lamellar phase. The lamellar phase can provide resistance to shear, adequate yield to suspend particles and droplets and at the same time providing long term stability, since it is thermodynamically stable. The lamellar phase tends to have a viscosity that minimizes the need for viscosity modifiers, but they can be included if desired.

Anionic surfactants can be either linear or branched. Examples of some suitable linear anionic surfactants include ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, sodium cocoyl isethionate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Examples of some suitable branched anionic surfactants include but are not limited to the following surfactants: sodium trideceth sulfate, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, sodium $C_{12-14}$ pareth-n sulfate, and combinations thereof. Other salts of all the aforementioned surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al on Jan. 1, 2002. Preferred alcohols are Safol™ 23 and Neodol™ 23. Preferred alkoxylated alcohols are Safol™ 23-3 and Neodol™ 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is a preferred sulfation process.

The anionic surfactant may also be STnS, wherein n can define average moles of ethoxylation. A structured cleansing phase can include from about 5% to about 20%, by weight of the personal care composition, of STnS. n can range from about 0 to about 3, from about 0.5 to about 2.7, from about 1.1 to about 2.5, from about 1.8 to about 2.2, or n can be about 2. When n is less than 3, STnS can provide improved stability, improved compatibility of benefit agents within the personal care compositions, and increased mildness of the personal care compositions, such described benefits of STnS are disclosed in U.S. Patent Application Publication No. 2012/0009285.

Further, the structured cleansing phase can comprise a structuring system, wherein the structuring system can comprise an associative polymer and a non-associative polymer. The structuring system can comprise from about 0.01% to about 5%, from about 0.05% to about 1%, from about 0.07% to about 0.5%, or from about 0.1% to about 0.3%, by weight of the personal care composition, of a non-associative polymer. The structuring system can comprise from about 0.001% to about 5%, from about 0.005% to about 0.5%, from about 0.007% to about 0.05%, from about 0.008% to about 0.04%, or from about 0.01% to about 0.03%, by weight of the personal care composition, of an associative polymer. As noted herein, stability of a personal care composition can be maintained or enhanced even with the reduction of associative polymer with the addition of a non-associative polymer.

Such associative polymers can be a crosslinked, alkali swellable, associative polymer comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in a presence of an electrolyte. The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis, or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, steareth, or other linear, branched, saturated, or unsaturated alkyl or alketh hydrocarbon side chains.

Associative polymers having certain % HM and certain carbon numbers of hydrophobic end groups of alkyl side chains may also provide significant enhancement of structure to structured surfactant compositions, especially to compositions comprising reduced levels of surfactant. Such associative polymers can also provide the above structure at surprisingly low levels of polymer structurant. Concentrations of associative polymer of up to about 5% or even 10% are taught in the art to obtain a sufficient amount structure (e.g., exemplary compositions of U.S. Pat. No. 7,119,059 (Librizzi, et al.) and U.S. Pat. No. 6,897,253 (Schmucker-Castner, et al.). Inventors have found when associative polymer % HM and an alkyl side chain number of carbons can be optimized, structure of an aqueous structured surfactant phase can be increased using only less than about 3 wt %, less than about 2%, less than about 1%, and less than about 0.2%, of an associative polymer, as a percentage of an aqueous structured surfactant phase.

The acidic monomer can comprise any acid functional group, for example sulfate, sulfonate, carboxylate, phosphonate, or phosphate or mixtures of acid groups. The acidic monomer can comprise, for example, a carboxylate, alternatively the acidic monomer is an acrylate, including acrylic acid and/or methacrylic acid. The acidic monomer comprises a polymerizable structure, e.g., vinyl functionality. Mixtures of acidic monomers, for example acrylic acid and methacrylic acid monomer mixtures, are useful.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl(meth) acrylate, where (meth)acrylate is understood to mean either methyl acrylate or acrylate, or mixtures of the two.

Sometimes, the hydrophobic end group of the associative polymer can be incompatible with the aqueous phase of the composition and can associate with lathering surfactant hydrophobe components. Without intending to be limited by theory, it is believed that longer alkyl chains of structuring polymer hydrophobe end groups can increase incompatibility with the aqueous phase to enhance structure, whereas somewhat shorter alkyl chains having carbon numbers closely resembling lathering surfactant hydrophobes (e.g., 12 to 14 carbons) or multiples thereof (for bilayers, e.g.) can also be effective. An ideal range of hydrophobic end group carbon numbers combined with an optimal percentage of hydrophobic monomers expressed as a percentage of the polymer backbone can provide increased structure to the lathering, structured surfactant composition at low levels of polymer structurant.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than about 1% HM. Associative polymers can comprise about $C_{16}$ (cetyl) alkyl hydrophobic side chains with about 0.7% hydrophobic modification, but a percentage hydrophobic modification can be up to an aqueous solubility limit in surfactant compositions (e.g., up to 2%, 5%, or 10%). Other associative polymers can include stearyl, octyl, decyl and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about $C_{18}$ (stearyl) side chains and about 0.4% HM, and AQUPEC® HV-701EDR which comprises about $C_8$ (octyl) side chains and about 3.5% HM, and mixtures thereof. Another exemplary associative polymer can be Stabylen 30 manufactured by 3V Sigma S.p.A., which has branched isodecanoate hydrophobic associative side chains.

As set forth above, the structured cleansing phase of a personal care composition can further include a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), and synthetic hydrocarbon polymers (e.g., polyacrylamide and copolymers, polyethylene oxide, polyacrylic acid copolymers).

Personal care compositions can additionally comprise a cationic deposition polymer in one or more phases as a deposition aid for benefit agents described herein. Non-limiting examples include those polymers disclosed in U.S. Pat. No. 6,649,155; U.S. Pat. No. 8,349,300; U.S. Patent Publication 2008/0206355; and U.S. Patent Publication No. 2006/0099167A1. The personal cleansing composition may comprise a cationic deposition polymer that forms a premix when added to the anionic microcapsules. The cationic deposition polymer may be included in the composition at a level from about 0.01% to about 2%, alternatively from about 1.5% to about 1.9%, alternatively from about 1.8% to about 2.0%. The cationic deposition polymer may be a water soluble polymer with a charge density from about 0.5 milliequivalents per gram to about 12 milliequivalents per gram. The cationic deposition polymer used in the composition may have a molecular weight of about 100,000 Daltons to about 5,000,000 Daltons. The cationic deposition polymer may be a low charge density cationic polymer.

The cationic deposition polymer may be a synthetic cationic deposition polymer. A variety of synthetic cationic deposition polymers can be used including mono- and di-alkyl chain cationic surfactants. In some examples, mono-alkyl chain cationic surfactants are chosen including, for example, mono-alkyl quaternary ammonium salts and mono-alkyl amines. In some examples, di-alkyl chain cationic surfactants are used and include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

The cationic deposition polymer may be a naturally derived cationic polymer. The term, "naturally derived cationic polymer" as used herein, refers to cationic deposition polymers which are obtained from natural sources. The natural sources include polysaccharide polymers. Therefore, the naturally derived cationic polymer may be selected from the group consisting of starches, guar, cellulose, Cassia, locust bean, Konjac, Tara, galactomannan, tapioca, and synthetic polymers. In a further embodiment, cationic deposition polymers are selected from Mirapol 100S (Rhodia), Jaguar C17, polyDADMAC, Tapioca starch (Akzo), poly-Triquat, and mixtures thereof.

The personal care composition can be optionally free of sodium lauryl sulfate, hereinafter SLS, and can comprise at least a 70% lamellar structure. However, in an alternative arrangement, the structured cleansing phase can comprise at least one surfactant, wherein the at least one surfactant includes SLS. Suitable examples of SLS are described in U.S. Patent Application Publication No. 2010/0322878.

A personal care composition can further comprise from about 0.1% to 20%, by weight of the personal care composition, of a cosurfactant. Cosurfactants can comprise amphoteric surfactants, zwitterionic surfactants, or mixtures thereof. A personal care composition can include an amphoteric surfactant and/or a zwitterionic surfactant. Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use can include those that are broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

Other suitable surfactants or cosurfactants that can generally be used in a structured cleansing phase for a personal care composition are described in McCutcheon's: Detergents and Emulsifiers North American Edition (Allured Publishing Corporation 1947) (1986), McCutcheon's, Functional Materials North American Edition (Allured Publishing Corporation 1973) (1992) and U.S. Pat. No. 3,929,678 (filed Aug. 1, 1974).

The structured cleansing phase of the personal care composition can also comprise water. The structured cleansing phase of the personal care composition can comprise from about 10% to about 90%, from about 40% to about 85%, or from about 60% to about 80%, by weight of the personal care composition, of water.

Other optional additives can be included in the cleaning phase, including for example an emulsifier (e.g., non-ionic emulsifier) and electrolytes. Suitable electrolytes can includes an anion such as phosphate, chloride, sulfate, citrate, and mixtures thereof and a cation such as sodium, ammonium, potassium, magnesium, and mixtures thereof. For example, suitable electrolytes can include sodium chloride, ammonium chloride, sodium sulfate, ammonium sulfate, and mixtures thereof. Other suitable emulsifiers and electrolytes are described in U.S. Patent Application Publication No. 2012/0009285.

B. Benefit Phase

As noted herein, personal care compositions can include a benefit phase. The benefit phase can be hydrophobic and/or anhydrous. The benefit phase can also be substantially free of or free of surfactant. The benefit phase can also include one or more benefit agents. In particular, the benefit phase can comprise from about 0.1% to about 50%, by weight of the personal care composition, of a benefit agent.

In some examples, the benefit phase includes triglycerides. In some examples, the triglyceride is provided as triglyceride oil. Non-limiting examples of triglyceride oils include olive oil, sunflower oil, soybean oil, peanut oil, rapeseed oil, almond oil, palm oil, coconut oil, palm kernel oil, and mixtures thereof.

In some examples, the benefit phase may also include one or more of following at levels that do not impair the development of the clusters of the microcapsules: castor oil, mineral oil, paraffin oil, petrolatum, lanolin and derivatives thereof, volatile and non-volatile organosiloxanes, waxes like montan wax, ceresine, a microcrystalline wax, hydroxyoctacosanyl hydroxystearate, beeswax, synthetic beeswax, and silicone wax.

C. Carrier

The compositions herein may be in the form of pourable liquids (under ambient conditions). Such compositions will therefore typically comprise a carrier, which may be present at a level of from about 20% to about 95%, or even from about 60% to about 85%. The carrier may comprise water, or a miscible mixture of water and organic solvent, and in some aspects may comprise water with minimal or no significant concentrations of organic solvent, except as otherwise incidentally incorporated into the composition as minor ingredients of other essential or optional components.

The carrier may include water and/or water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

D. Microcapsules

The personal care compositions herein may include microcapsules in the cleansing and/or benefit phases. The microcapsules may be any kind of microcapsule disclosed herein or known in the art. The microcapsules may have a shell and a core material encapsulated by the shell. The core material of the microcapsules may include one or more fragrances. The shells of the microcapsules may be made from synthetic polymeric materials or naturally-occurring polymers. Synthetic polymers may be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Natural polymers occur in nature and may often be extracted from natural materials. Non-limiting examples of naturally occurring polymers are silk, wool, gelatin, cellulose, proteins, and combinations thereof.

The microcapsules may be friable microcapsules. A friable microcapsule is configured to release its core material when its shell is ruptured. The rupture may be caused by forces applied to the shell during mechanical interactions. The microcapsules may have a shell with a volume weighted fracture strength of from about 0.2 mega Pascals to about 15.0 mega Pascals, when measured according to the Fracture Strength Test Method described herein, or any incremental value expressed in 0.1 mega Pascals in this range, or any range formed by any of these values for fracture strength. As an example, a microcapsule may have a shell with a volume weighted fracture strength of 0.8-15.0 mega Pascals (MPa), alternatively from 5.0-12.0 mega Pascals (MPa), or alternatively from 6.0-10.0 mega Pascals (MPa).

The microcapsules may have a median volume-weighted particle size of from 2 microns to 80 microns, from 10 microns to 30 microns, or from 10 microns to 20 microns. The microcapsules may have various core material to shell weight ratios. The microcapsules may have a core material to shell ratio that is greater than or equal to: 70% to 30%, 75% to 25%, 80% to 20%, 85% to 15%, 90% to 10%, and 95% to 5%.

The microcapsules may have shells made from any material in any size, shape, and configuration known in the art. Some or all of the shells may include a polyacrylate material, such as a polyacrylate random copolymer. For example, the polyacrylate random copolymer may have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, and the shell has an overall mass, the polyacrylate material may form 5-100% of the overall mass, or any integer value for percentage in this range, or any range formed by any of these values for percentage. As examples, the polyacrylate material may form at least 5%, at least 10%, at least 25%, at least 33%, at least 50%, at least 70%, or at least 90% of the overall mass.

Some or all of the microcapsules may have various shell thicknesses. For at least a first group of the provided microcapsules, each microcapsule may have a shell with an overall thickness of 1-300 nanometers, or any integer value for nanometers in this range, or any range formed by any of these values for thickness. As an example, microcapsules may have a shell with an overall thickness of 2-200 nanometers.

The microcapsules may also encapsulate one or more benefit agents. The benefit agent(s) include, but are not limited to, cooling sensates, warming sensates, fragrances, oils, pigments, phase change materials, and other kinds of benefit agent known in the art, in any combination. In some examples, the fragrance encapsulated may have a C log P of less than 4.5 or a C log P of less than 4. Alternatively the fragrance encapsulated may have a C log P of less than 3. In some examples, the microcapsule may be anionic, cationic, zwitterionic, or have a neutral charge. The benefit agents(s) may be in the form of solids and/or liquids. The benefit agent(s) may be any kind of fragrance(s) known in the art, in any combination.

The microcapsules may encapsulate a partitioning modifier in addition to the benefit agent. Non-limiting examples of partitioning modifiers include mono, di- and tri-esters of $C_4$-$C_{24}$ fatty acids and glycerin; isopropyl myristate, soybean oil, hexadecanoic acid, methyl ester, isododecane, and combinations thereof, in addition to the encapsulated. The oil soluble material may have a C log P about 4 or greater, at least 5 or greater, at least 7 or greater, or at least 11 or greater. Microcapsules may also have varying ratios of the partitioning modifier to the benefit so as to make different populations of microcapsules that may have different bloom patterns. Such populations may also incorporate different perfume oils so as to make populations of microcapsules that display different bloom patterns and different scent experiences.

The microcapsule's shell may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules may include a core material and a shell surrounding the core material, wherein the shell comprises: a plurality of amine monomers selected from the group consisting of aminoalkyl acrylates, alkyl aminoalkyl acrylates, dialkyl aminoalkyl acrylates, aminoalkyl methacrylates, alkylamino aminoalkyl methacrylates, dialkyl aminoalkyl methacrylates, tertiarybutyl aminethyl methacrylates, diethylaminoethyl methacrylates, dimethylaminoethyl methacrylates, dipropylaminoethyl methacrylates, and mixtures thereof; and a plurality of multifunctional monomers or multifunctional oligomers.

Processes for making microcapsules are well known. Various processes for microencapsulation, and exemplary methods and materials, are set forth in U.S. Pat. No. 6,592,990; U.S. Pat. No. 2,730,456; U.S. Pat. No. 2,800,457; U.S. Pat. No. 2,800,458; U.S. Pat. No. 4,552,811; and U.S. 2006/0263518 A1. U.S. Patent Publication Nos. 2012/0276175, 2011/0268802, 2011/0269657, 2011/0269658, 2011/268778 are also hereby incorporated by reference.

In some examples, the microcapsules may be made by using a process comprising the steps of: 1) preparing an oligomeric composition comprising the reaction product of, or obtainable by reacting together: a) a polyamine component in the form of melamine or of a mixture of melamine and at least one C1-4 compound comprising two NH2 functional groups; b) an aldehyde component in the form of a mixture of glyoxal, a $C_{4-6}$ 2,2-dialkoxyethanal and optionally a glyoxalate, said mixture having a molar ratio glyoxal/$C_{4-6}$ 2,2-dialkoxy-ethanal comprised between about 1/1 and 10/1; and c) a protic acid catalyst; 2) preparing an oil-in-water dispersion, wherein the droplet size is comprised between 1 and 600 mih, and comprising: i) an oil; ii) a water medium; iii) at least an oligomeric composition as obtained in step 1); iv) at least a cross-linker selected amongst: A) C4-Ci2 aromatic or aliphatic di- or tri-isocyanates and their biurets, triurets, trimers and trimethylol propane-adduct; and/or B) a di- or tri-oxiran compounds of formula A-(oxiran-2-ylmethyl) n wherein n stands for 2 or 3 and A represents a $C_2$-$C_6$ group optionally comprising from 2 to 6 nitrogen and/or oxygen atoms; v) optionally a C1-4 compound comprising two NH2 functional groups; 3) heating said dispersion; 4) cooling said dispersion; and 5) optionally adding to the dispersion of step 4) at least one cationic polymer and/or urea or ethylene urea; and 6) optionally drying the final dispersion to obtain the dried core-shell microcapsule. The microcapsules described in the following publications/patents are also hereby incorporated by reference: U.S. Pat. No. 8,835,002 and U.S. Patent Publication No. 2014/0322283.

In some examples, the microcapsules may be prepared by the following: 1) preparing an oligomeric composition comprising the reaction product of, or obtainable by reacting together: a) a polyamine component in the form of melamine or of a mixture of melamine and at least one $C_{1-4}$ compound comprising two $NH_2$ functional groups; b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between about 1/1 and 10/1; and c) a protic acid catalyst; 2) preparing an oil-in-water dispersion, wherein the droplet size is comprised between 1 and 600 µm, and comprising: i) an oil; ii) a water medium; iii) at least an oligomeric composition as obtained in step 1); iv) at least a cross-linker selected amongst: A) $C_4$-$C_{12}$ aromatic or aliphatic di- or tri-isocyanates and their biurets, triurets, trimers and trimethylol propane-adduct; and/or B) a di- or tri-oxiran compounds of formula A-(oxiran-2-ylmethyl)$_n$ wherein n stands for 2 or 3 and A represents a $C_2$-$C_6$ group optionally comprising from 2 to 6 nitrogen and/or oxygen atoms; v) optionally a $C_{1-4}$ compound comprising two $NH_2$ functional groups; 3) heating said dispersion; 4) cooling said dispersion; and 5) optionally adding to the dispersion of step 4) at least one cationic polymer and/or urea or ethylene urea; and 6) optionally drying the final dispersion to obtain the microcapsule.

The microcapsules may also be prepared by: 1) preparing an oil-in-water dispersion, wherein the droplet size is comprised between 1 and 600 µn, and comprising at least an oligomeric composition as defined below; 2) optionally adding to the dispersion a C compound comprising two $NH_2$ functional groups; 3) heating said dispersion; 4) cooling said dispersion; and 5) optionally drying the final dispersion to obtain the microcapsule. The oligomeric composition may be prepared by a reaction comprising: 1) a poly amine component in the form of melamine or of a mixture of melamine and at least one C compound comprising two N3/4 functional groups; 2) an aldehyde component in the form of a mixture of glyoxal, a $C_4$_6 2,2-dialkoxy-ethanal and optionally a glyoxalate, said mixture having a molar ratio glyoxal/$C_4$-6 2,2-dialkoxy-ethanal comprised between about 1/1 and 10/1; and 3) a protic acid catalyst. "Glyoxal" is understood to mean both the free di-aldehyde form (e.g. OHC—CHO) and the hydrated forms (e.g. $(HO)_2HC$—CHO). "Glyoxalate" is understood to mean the glyoxalic acid or an alkaline salt of glyoxalic acid (such as OHC—COONa or OHC—COOK) or mixture thereof. The term "glyoxalate" is also understood to mean both the free aldehyde form (i.e. OHC—COOH) and the hydrated form (e.g. $(HO)_2HC$—COOH or $(HO)_2HC$—COONa). Non-limiting examples of C compound comprising two NH2 functional groups include urea, IH—I,2,4-triazole-3,5-diamine and mixtures thereof.

The microcapsule may be spray-dried to form spray-dried microcapsules. The composition may also contain one or more additional delivery systems for providing one or more benefit agents, in addition to the microcapsules. The additional delivery system(s) may differ in kind from the microcapsules. For example, wherein the microcapsule encapsulates a fragrance, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), starch derivatives, and combinations thereof. Said polysaccharide material may or may not be modified.

The compositions may also include a parent fragrance and one or more encapsulated fragrances that may or may not differ from the parent fragrance. For example, the composition may include a parent fragrance and a non-parent fragrance. A parent fragrance refers to a fragrance that is dispersed throughout the composition and is typically not encapsulated when added to the composition. Herein, a non-parent fragrance refers to a fragrance that differs from a parent fragrance included within the composition and is encapsulated with an encapsulating material prior to inclusion into the composition. Non-limiting examples of differences between a fragrance and a non-parent fragrance include differences in chemical make-up.

Other Ingredients

Additional other ingredients can also be added to the personal care composition for treatment of the skin, or to modify the aesthetics of the personal care composition as is the case with perfumes, colorants, dyes or the like. Optional materials useful in products herein can be categorized or described by their cosmetic and/or therapeutic benefit or their postulated mode of action or function. However, it can be understood that actives and other materials useful herein can, in some instances, provide more than one cosmetic and/or therapeutic benefit or function or operate via more than one mode of action. Therefore, classifications herein can be made for convenience and cannot be intended to limit an ingredient to particularly stated application or applications listed. A precise nature of these optional materials, and levels of incorporation thereof, will depend on the physical form of the composition and the nature of the cleansing operation for which it is to be used. The other materials can usually be formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less of the personal care composition.

To further improve stability under stressful conditions such as high temperature and vibration, densities of separate phases can be adjusted such that they can be substantially equal. To achieve this, low density microspheres can be added to one or more phases of the personal care composition. Examples of personal care compositions that comprise low density microspheres are described in a patent application published on May 13, 2004 under U.S. Patent Publication No. 2004/0092415A1 entitled "Striped Liquid Personal Cleansing Compositions Containing A Cleansing Phase and A Separate Phase with Improved Stability," filed on Oct. 31, 2003 by Focht, et al.

Other non-limiting ingredients that can be used in the personal care compositions include components that can be selected from the group consisting of thickening agents; preservatives; antimicrobials; fragrances; chelators (e.g., such as those described in U.S. Pat. No. 5,487,884 issued to Bisset, et al.); sequestrants; vitamins (e.g., Retinol); vitamin derivatives (e.g., tocophenyl actetate, niacinamide, panthenol); sunscreens; desquamation actives (e.g., such as those described in U.S. Pat. Nos. 5,681,852 and 5,652,228 issued to Bisset); anti-wrinkle/anti-atrophy actives (e.g., N-acetyl derivatives, thiols, hydroxyl acids, phenol); anti-oxidants (e.g., ascorbic acid derivatives, tocophenol) skin soothing agents/skin healing agents (e.g., panthenoic acid derivatives, aloe vera, allantoin); skin lightening agents (e.g., kojic acid, arbutin, ascorbic acid derivatives) skin tanning agents (e.g., dihydroxyacteone); anti-acne medicaments; essential oils; sensates; pigments; colorants; pearlescent agents; interference pigments (e.g., such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g., talc, kolin, mica, smectite clay, cellulose powder, polysiloxane, silicas, carbonates, titanium dioxide, polyethylene beads) hydrophobically modified non-platelet particles (e.g., hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. The multiphase personal care composition can comprise from about 0.1% to about 4%, by weight of the personal care composition, of hydrophobically modified titanium dioxide. Other such suitable examples of such skin actives are described in U.S. Patent Application Publication No. 2012/0009285. Other ingredients can be most typically those materials approved for use in cosmetics and that are described in the CTFA Cosmetic Ingredient Handbook, Second Edition, The Cosmetic, Toiletries, and Fragrance Association, Inc. 1988, 1992.

III. Forming a Premix

The cationic deposition polymer and the anionic microcapsule are mixed to form a premix before addition to the personal cleansing composition comprising at least one anionic surfactant and a carrier.

The weight ratio of the anionic microcapsule to the cationic deposition polymer (based on the dry weight of the anionic microcapsules and the dry weight of the cationic deposition polymer) is from about 0.5:30 to about 20:1, from about 5:15 to about 15:1, and from about 5:1 to about 12:1. It is believed that too much cationic polymer may not provide enhanced and/or prolonged benefits to the benefit agent microcapsules due to the formation of excess cationic polymer coating on the capsule wall. This excess coating may prevent the microcapsule wall from breaking and releasing the benefit agents.

The cationic deposition polymer may include those listed above with respect to the structured cleansing phase. The cationic deposition polymer premixed with the microcapsule may be the same or different than any included in the structured cleansing phase. The cationic deposition polymer can be, for example, polyvinyl formamide. The microcapsule can be premixed to form a slurry comprising, by weight of the slurry, from about 0.01% to about 5%, from about 0.05% to about 2% or even from about 0.1% to about 1%, of a polyvinyl formamide; from about 0% to about 5% $MgCl_2$; from about 0% to about 1% xanthan gum; and a carrier.

The cationic deposition polymer for use in the microcapsule premix can have a molecular weight from about 1,000 Da to about 50,000,000 Da; from about 5,000 Da to about 25,000,000 Da; from about 10,000 Da to about 10,000,000 Da; or even from about 300,000 Da to about 2,000,000. The cationic deposition polymer can also have a charge density from about 1 meq/g to about 23 meq/g, from about 1 meq/g to about 16 meq/g, from about 1 meq/g to about 10 meq/g, or from 1 meq/g to about 4 meq/g.

IV. Method of Manufacture

The personal cleansing compositions herein may be prepared by a process comprising: 1) combining an anionic microcapsule with a cationic deposition polymer to form a premix; and 2) adding the premix to a composition comprising a surfactant, a benefit agent comprising a triglyceride, and a carrier.

V. Product Forms

The personal cleansing compositions may be in the form of rinse-off products or leave-on products, and can be formulated in a wide variety of product forms, including but not limited to creams, gels, emulsions, mousses, body washes, shampoos, conditioners, and sprays.

As noted herein, the personal cleansing composition may include a structured cleansing phase and a benefit phase. In some examples, the structured cleansing phase and the benefit phase are in physical contact. In some examples, the personal cleansing composition may be a multiphase personal cleansing composition where the structured cleansing phase and the benefit phase are be blended or mixed to a significant degree, but remain physically distinct such that the physical distinctiveness is undetectable to the naked human eye.

In some examples, the personal cleansing composition may be a multiphase personal cleansing composition where the structured cleansing phase and the benefit phase are made to occupy separate but distinct physical spaces inside a package in which the phases are stored. In such examples, the structured cleansing phase and the benefit phase can be stored such that the phases are not in direct contact with one another. In some examples, the personal cleansing composition can be a multiphase personal cleansing composition where the structured cleansing phase and the benefit phase are in physical contact and have a striped or marbled configuration.

In some examples, the personal cleansing composition can include a combination of one or more of the above multiphase personal cleansing compositions. In some examples, one blended multiphase personal cleansing composition can be stacked as stripes with another blended multiphase personal cleansing composition. And in other examples, the blended multiphase personal cleansing compositions distinguishable by color can be stacked as stripes wherein the blended multiphase personal cleansing compositions can be otherwise similar.

VI. Test Methods

It is understood that the test methods that are disclosed in the Test Methods Section of the present application should be used to determine the respective values of the parameters of Applicants' invention as such invention is described and claimed herein.

C log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). C log P values may be calculated by using the "C LOG P"

program available from Daylight Chemical Information Systems Inc. of Irvine, Calif. U.S.A.

Boiling Point

Boiling point is measured by ASTM method D2887-04a, "Standard Test Method for Boiling Range Distribution of Petroleum Fractions by Gas Chromatography," ASTM International.

Zeta Potential (1) Equipment specifications: Malvern Zeatasizer Nano Model ZEN3600 Sample cell, disposable capillary cell (green cell)
(2) Use Duke standards to measure the PSD, and use it to measure the zeta potential to assure that the instrument is functioning properly.
(3) Flush a DTS1060 capillary cell with 1-2 mL ethanol, then with DI water to prepare the capillary cell.
(4) Sample preparation: first, filter 20 mL DI water through 0.2 micron filter into a 20 mL vial. Add 1 drop (50 microliters of 30 wt % solids suspension into the vial and invert the sample back and forth gently until the particulate suspension is homogeneously dispersed in the vial. Next, rinse a DTS1060 green disposable zeta cell with 1-2 mL of DI water, then use a syringe to transfer the sample solution from the vial into the zeta cell, making sure that no air bubbles are present in the cell. Fill the cell to the top, then place a cap on the cell outlet and inlet (again making sure no air bubbles are present in the sample cell). Then, place the cell in the sample chamber, with the electrodes facing the sides of the system. Finally, place the sample cell in the instrument.
(5) Conditions for the run:
   a. Refractive index=1.35 (this number may vary for suspensions. One can measure the refractive index for any particulate suspension using a refractometer)
   b. Temperature=25 degrees Centigrade
   c. Equilibration time=1 minute
   d. Smoluchowski model to be used to calculate the zeta potential
(6) Measure each sample in triplicate. The result from the instrument is reported as Zeta Potential in milliVolts, with no extrapolation.

VII. Examples

The following examples illustrate the present invention. The exemplified compositions may be prepared by conventional formulation and mixing techniques. It will be appreciated that other modifications of the present invention within the skill of those in the art may be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of microcapsules and compositions described herein.

| I: Personal Care Composition | Example A | Example B | Example C |
|---|---|---|---|
| Sodium Trideceth Sulfate (sulfated from Trideceth-2, Stepan) | 9.59% | 9.08% | 9.08% |
| Cocoamidopropyl Betaine | 2.87% | 2.71% | 2.71% |
| Trideceth-3 | 1.53% | 1.45% | 1.45% |
| Sodium Chloride | 4.42% | 4.19% | 4.19% |
| Guar Hydroxypropyltrimonium Chloride (N-Hance CG-17 from Aqualon) | 0.50% | 0.47% | 0.47% |
| Xanthan Gum (Keltrol 1000 from CP Kelco) | 0.34% | 0.32% | 0.32% |
| Acrylates/C10-30 Alkylacrylate Cross Polymer (Aqupec SER-300C from Sumitomo) | 0.03% | 0.029% | 0.029% |
| Methyl chloro isothiazolinone and methyl isothiazolinone (Kathon CG, Rohm & Haas) | 0.033% | 0.033% | 0.033% |
| EDTA (Dissolvine NA 2x) | 0.31% | 0.31% | 0.31% |
| Sodium Benzoate | 0.14% | 0.14% | 0.14% |
| Perfume | 1.0% | 1.0% | 1.0% |
| RBD Soybean Oil | 4.85% | 9.70% | — |
| Glyceryl Oleate | 0.05% | 0.10% | 0.20% |
| BHT | 0.1% | 0.20% | — |
| Petrolatum | — | — | 9.8% |
| Perfume Microcapsule Slurry of Examples 1, 2, 3, 4 or 5 | 0.8% | 0.8% | 0.8% |
| Citric Acid, titrate | pH = 5.7 ± 0.2 | pH = 5.7 ± 0.2 | pH = 5.7 ± 0.2 |
| Water and minors | Q.S. | Q.S. | Q.S. |

Example 1. Nonionic Microcapsule

An oil solution, consisting of 75 g Fragrance Oil scent A, 75 g of Isopropyl Myristate, 0.6 g DuPont Vazo-52, and 0.4 g DuPont Vazo-67, is added to a 35° C. temperature controlled steel jacketed reactor, with mixing at 1000 rpm (4 tip, 2" diameter, flat mill blade) and a nitrogen blanket applied at 100 cc/min. The oil solution is heated to 75° C. in 45 minutes, held at 75° C. for 45 minutes, and cooled to 60° C. in 75 minutes. A second oil solution, consisting of 37.5 g Fragrance Oil, 0.5 g tertiarybutylaminoethyl methacrylate, 0.4 g 2-carboxyethyl acrylate, and 20 g Sartomer CN975 (hexafunctional urethane-acrylate oligomer) is added when the first oil solution reached 60° C. The combined oils are held at 60° C. for an additional 10 minutes. Mixing is stopped and a water solution, consisting of 56 g of 5% active polyvinyl alcohol Celvol 540 solution in water, 244 g water, 1.1 g 20% NaOH, and 1.2 g DuPont Vazo-68WSP, is added to the bottom of the oil solution, using a funnel. Mixing is again started, at 2500 rpm, for 60 minutes to emulsify the oil phase into the water solution. After milling is completed, mixing is continued with a 3" propeller at 350 rpm. The batch is held at 60° C. for 45 minutes, the temperature is increased to 75° C. in 30 minutes, held at 75° C. for 4 hours, heated to 90° C. in 30 minutes and held at 90° C. for 8 hours. The batch is then allowed to cool to room temperature. The finished microcapsules have a median particle size of 6.4 microns, a broadness index of 1.3, and a zeta potential of negative 0.5 millivolts, and a total scent A concentration of 27.6 wt %.

Example 2. Anionic Microcapsule, Large Particle Size

Capsules are made using identical materials, compositions, and process conditions as in Example 1 with the following exceptions: 1 gram of Vazo-52, 0.8 grams of Vazo-67, 0.3 grams of tertiarybutylaminoethyl methacrylate, 0.25 grams of 2-carboxyethyl acrylate, and 12 grams of Sartomer CN975 as compositional differences in the oil phase; and 22 grams of 25% active Colloid 351, and 308 grams of water as compositional differences in the water phase. All other mixing and process conditioner remains the same. The finished microcapsules have a median particle size of 10.7 microns, a broadness index of 1.5, and a zeta potential of negative 60 milivolts, and a total scent A concentration of 34.9 wt %.

Example 3. Anionic Microcapsule, Small Particle Size

Capsules are made using identical materials, compositions, and process conditions as in Example 1 with the following exceptions: 1 gram of Vazo-52, 0.8 grams of Vazo-67, 1.5 grams of tertiarybutylaminoethyl methacrylate, 1.2 grams of 2-carboxyethyl acrylate, and 60 grams of Sartomer CN975 as compositional differences in the oil phase; and 68 grams of 25% active Colloid 351, and 282 grams of water as compositional differences in the water phase. All other mixing and process conditioner remains the same. The finished microcapsules have a median particle size of 1.4 microns, a broadness index of 1.2, and a zeta potential of negative 60 milivolts, and a total scent A concentration of 20.7 wt %.

Example 4. Anionic Microcapsule

Capsules are made using identical materials, compositions, and process conditions as in Example 2 with the following exceptions: 1 gram of tertiarybutylaminoethyl methacrylate, 0.8 grams of 2-carboxyethyl acrylate, and 40 grams of Sartomer CN975 as compositional differences in the oil phase; and 22 grams of 25% active Colloid 351, and 282 grams of water as compositional differences in the water phase. All other mixing and process conditioners remain the same. The finished microcapsules have a median particle size of 4.8 microns, a broadness index of 1.3, and a zeta potential of negative 60 milivolts, and a total scent A concentration of 23.5 wt %.

Example 5. 90 wt % Core/10 wt % Wall, Scent A Capsules, 20% Partitioning Modifier An oil solution, consisting of 128.4 g of perfume Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This mixture is hereafter referred to as oil solution A.

In a reactor vessel, an aqueous solution is prepared consisting of 300 g of deionized water to which is dispersed in 2.40 grams of Celvol 540 polyvinyl alcohol at 25° C. The mixture is heated to 85° C. and held there for 45 minutes. The solution is cooled to 30° C. 1.03 grams of Wako Chemicals V-501 initiator is added, along with 0.51 grams of a 40% sodium hydroxide solution. The solution is then heated to 50° C., and the solution is maintained at that temperature.

To oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This mixture is hereafter referred to as oil solution B. Use a Caframo mixer with a 4-blade pitched turbine agitator.

Start a nitrogen blanket on top of the aqueous solution in reactor. Start transferring oil solution B into the aqueous solution in the reactor with minimal mixing. Increase the agitation of mixing to 1800-2500 rpm for a period of 60 minutes to emulsify the oil phase into the water solution. After milling is completed, mixing is continued with a 3" propeller at 350 rpm. The batch is then held at 50° C. for 45 minutes. The temperature is then increased to 75° C. in 30 minutes, held at 75° C. for 4 hours, heated to 95° C. in 30 minutes and held at 95° C. for 6 hours. The batch is then allowed to cool to room temperature.

A perfume encapsulated, called Scent A, is utilized to prepare Examples 1-5. The table below lists the ingredients, and their properties. Table 5 provides the C log P breakdown of the perfume oil encapsulated.

| Scent A | ClogP | Dispersion $(MPa^{1/2})$ | H-Bond $(MPa^{1/2})$ | Polarity $(MPa^{1/2})$ | Boiling Point (° C.) |
|---|---|---|---|---|---|
| 3,6-Nonadien-1-ol | 2.45 | 15.76 | 14.28 | 4.39 | 213 |
| Allyl Caproate | 3.03 | 15.63 | 6.25 | 4.13 | 198 |
| Allyl Heptoate | 3.57 | 15.6 | 6.04 | 3.81 | 216 |
| Beta Gamma Hexenol | 1.3 | 15.79 | 14.73 | 5.45 | 155 |
| Cis 3 Hexenyl Acetate | 2.18 | 15.75 | 6.57 | 4.55 | 167 |
| Cis-6-Nonen-1-OL FCC | 2.7 | 15.78 | 13.46 | 4.01 | 214 |
| Cyclo Galbanate | 2.54 | 17.15 | 6.84 | 3.9 | 273 |
| Cymal | 3.62 | 17.88 | 4.16 | 5.6 | 290 |
| Dihydro Myrcenol | 3.08 | 15.54 | 10.78 | 3.6 | 195 |
| Dimethyl Benzyl Carbinyl Butyrate | 4.09 | 17.76 | 4.39 | 4.99 | 270 |
| Ethyl 2 Methyl Pentanoate | 2.55 | 15.58 | 5.97 | 3.64 | 157 |
| Ethyl Acetoacetate | 0.15 | 16.16 | 8.7 | 8.12 | 179 |
| Ethyl Caproate FCC | 2.62 | 15.86 | 6.26 | 3.61 | 165 |
| Ethyl Maltol | 0.17 | 18.14 | 9.66 | 6.3 | 274 |
| Ethyl Oenanthate | 3.2 | 15.71 | 6.09 | 3.27 | 183 |
| Ethyl-2-Methyl Butyrate | 1.91 | 15.68 | 6.18 | 3.92 | 133 |
| Florhydral | 3.59 | 18.04 | 4.19 | 5.57 | 295 |
| Hexamethylindanopyran | 5.43 | 15.68 | 3.59 | 6.11 | 398 |
| Gamma Decalactone | 3.23 | 17.32 | 6.36 | 11.78 | 211 |
| Hexyl Acetate | 2.64 | 15.86 | 6.44 | 3.7 | 165 |
| Ionone Beta | 4.02 | 16.54 | 4.37 | 5.65 | 267 |
| Jasmolactone | 2.36 | 17.59 | 6.44 | 6.47 | 219 |
| Liffarome | 2.14 | 15.61 | 7.32 | 3.23 | 167 |
| Ligustral Or Triplal | 1.78 | 17.28 | 5.13 | 7.17 | 199 |
| Linalool | 2.44 | 15.38 | 11.14 | 3.72 | 204 |
| Melonal | 2.09 | 15.55 | 4.86 | 6.65 | 182 |
| Nectaryl | 4.18 | 17.76 | 4.33 | 8.31 | 319 |
| Para Hydroxy Phenyl Butanone | 1.58 | 18.62 | 12.32 | 8.72 | 294 |
| Pino Acetaldehyde | 2.98 | 17.06 | 4.96 | 6.03 | 261 |
| Prenyl Acetate | 1.12 | 15.42 | 6.37 | 5.32 | 145 |
| Thesaron | 3.84 | 16.65 | 5.07 | 4.57 | 216 |
| Undecalactone | 3.75 | 17.24 | 6.21 | 11.1 | 228 |
| Undecavertol | 3.06 | 15.41 | 10.39 | 3.49 | 242 |
| Verdox | 3.87 | 16.96 | 5.34 | 3.66 | 223 |
| Verdural B Extra | 3.21 | 15.46 | 5.71 | 3.74 | 193 |

Examples D-L

The base surfactant composition can be prepared by standard mixing technique. First, add water to a container. Then, add the following ingredients with continuous mixing: sodium chloride, guar hydroxypropyl trimoium chloride, cocoamidopropyl betaine, sodium trideceth sulfate sodium lauryl sulfate. Prepare a premix of acrylates/C10-C30 alkylacrylates cross polymer and Xanthan gum with trideceth-3. Add the premix to the main container with mixing. Add EDTA, sodium Benzoate to the main container. Adjust the pH to 5.7 using 50% citric acid solution. Add Kathon CG. Keep mixing until homogeneous.

| Base Surfactant | |
|---|---|
| Sodium Trideceth Sulfate (sulfated from Trideceth-2, Stepan) | 10.3% |
| Cocoamidopropyl Betaine | 3.08% |
| Trideceth-3 | 1.64% |
| Sodium Chloride | 4.75% |
| Guar Hydroxypropyltrimonium Chloride (N-Hance CG-17 from Aqualon) | 0.53% |
| Xanthan Gum (Keltrol 1000 from CP Kelco) | 0.37% |
| Acrylates/C10-30 Alkylacrylate Cross Polymer (Aqupec SER-300C from Sumitomo) | 0.033% |
| Methyl chloro isothiazolinone and methyl isothiazolinone (Kathon CG, Rohm & Haas) | 0.0007% |
| EDTA (Dissolvine NA 2x) | 0.15% |
| Sodium Benzoate | 0.34% |
| Citric Acid, titrate | pH = 5.7 |
| Water and Minors | Q. S. |

Examples D-L can be prepared with standard mixing techniques. First, add the base surfactant to a container. Then, prepare a premix of soybean oil, glyceryl monooleate, BHT in a separate container by heating to 50° C. with mixing. Then, add the premix to the surfactant phase with continuous mixing. Then add the perfume, and PMC slurry (where utilized) into the batch. Keep mixing until homogenous.

| | Example D | Example E | Example F |
|---|---|---|---|
| I) Base Surfactant | 91.8% | 91.8% | 91.8% |
| II) Lipid Phase | | | |
| RBD Soybean Oil | 6.79% | 6.79% | 6.79% |
| Glyceryl Oleate | 0.07% | 0.07% | 0.07% |
| BHT | 0.14% | 0.14% | 0.14% |
| III) Perfume and PMC | | | |
| Neat Perfume | 1.2% | 1.0% | 1.0% |
| Perfume Microcapsule A (anionic microcapsules) | — | 0.2% | — |
| Perfume Microcapsule B (premix containing anionic microcapsules & cationic polymer) | — | — | 0.2% |
| Arm Wash Perfume Headspace Testing Results | | | |
| Initial Perfume GC Headspace (index to No Microcapsule Control) | 1 | 1.3 | 1.9 |
| Perfume GC Headspace after one Hour (pre-rub) (index to No Microcapsule Control) | 1 | 1.4 | 1.3 |
| Perfume GC Headspace after one Hour (post-rub) (index to No Microcapsule Control) | 1 | 1.5 | 10.6 |
| Product to Water Dilution (1:9) Ratio | | | |
| Optical Microscopy (10x DIC Mode) | Lipid Coacervate Only | Observed individual microcapsules floating in aqueous solution | Observed microcapsule clusters within the lipid/polymer coacervate |

| | Example G No PMC Control | Example H | Example I | Example J | Example K | Example L |
|---|---|---|---|---|---|---|
| IV) Base Surfactant | 91.8% | 91.37% | 91.29% | 91.37% | 91.27% | 91.27% |
| V) Lipid Phase | | | | | | |
| RBD Soybean Oil | 6.79% | 6.79% | 6.79% | 6.79% | 6.79% | 6.79% |
| Glyceryl Oleate | 0.07% | 0.07% | 0.07% | 0.07% | 0.07% | 0.07% |
| BHT | 0.14% | 0.14% | 0.14% | 0.14% | 0.14% | 0.14% |

-continued

| VI) Perfume and PMC | | | | | | |
|---|---|---|---|---|---|---|
| Neat Perfume | 1.2% | 1.0% | 1.0% | 1.0% | 1.0% | 1.0% |
| Perfume Microcapsule A (based on total oil content) (anionic PMC) | — | 0.63% (0.2% oil) | — | — | — | — |
| Perfume Microcapsule B (based on total oil content) (nonionic PMC) | | | 0.71% (0.2% oil) | | | |
| Perfume Microcapsule C (based on total oil content) (cationic PMC) | | | | 0.63% (0.2% oil) | | |
| Perfume Microcapsule D (based on total oil content) (anionic PMC + cationic polymer) | | | | | 0.73% (0.2% oil) | |
| Perfume Microcapsule E (based on total oil content) (anionic PMC + cationic polymer) Product to Water Dilution (1:9) Ratio | | | | | | 0.73% (0.2% oil) |
| Optical Microscopy (10x DIC Mode) PMC Clustering with Coacervate | No PMC Control | No Clustering | No Clustering | No Clustering | Yes | Yes |
| Corresponding FIG. | 1 | 2 | 3 | 4 | 5 | 6 |

Additional information on the microcapsules utilized in Examples H-L is listed below.

| Perfume Microcapsule A (anionic PMC) Properties | |
|---|---|
| Particle size (volume average) | 11.43 microns |
| Particle size distribution (volume average) | 1.75 |
| pH | 5.82 |
| % Total Oil | 31.58% |
| % Solids | 44.65% |
| Core Description | 80/20 Perfume/ Isopropyl Myristate |
| Core/Wall Ratio | 90/10 |
| Colloid Descriptor | 0.8% PVOH |
| Others | All beta C—anionic |
| Perfume Microcapsule B (nonionic PMC) Properties | |
| Particle size (volume average) | 11.15 microns |
| Particle size distribution (volume average) | 1.59 |
| pH | 5.57 |
| % Total Oil | 28.15% |
| % Solids | 46.30% |
| Core Description | 70/30 Perfume/ Isopropyl Myristate |
| Core/Wall Ratio | 90/10 |
| Colloid Descriptor | 0.8% PVOH |
| Others | CN975/TBAEMA/ Beta-C |
| Perfume Microcapsule C (cationic PMC) Properties | |
| Particle size (volume average) | 11.15 microns |
| Particle size distribution (volume average) | 1.79 |
| pH | 6.18 |
| % Total Oil | 31.86% |
| % Solids | 45.03% |
| Core Description | 80/20 Perfume/ Isopropyl Myristate |
| Core/Wall Ratio | 90/10 |
| Colloid Descriptor | 0.8% PVOH |
| Others | All TB AEMA- cationic |
| Perfume Microcapsule D (anionic PMC + cationic polymer) | |
| Particle size (volume average) | 19.66 microns |
| Particle size distribution (volume average) | 1.56 |
| pH | 5.28 |
| % Total Oil | 27.26% |
| Shell Descriptor | Melamine Formaldehyde |
| Cationic Deposition Polymer: Polyvinyl Formamide | 0.58% |
| Perfume Microcapsule E (anionic PMC + cationic polymer) | |
| Particle size (volume average) | 17.64 microns |
| Particle size distribution (volume average) | 1.54 |
| pH | 5.33 |
| % Total Oil | 27.29% |
| Shell Descriptor | Melamine Formaldehyde |
| Cationic Deposition Polymer: Polyvinyl Formamide | 0.58% |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular arrangements of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a microcapsule-containing personal care composition comprising:
    making a benefit phase comprising at least one triglyceride oil selected from the group consisting of olive oil, sunflower oil, soybean oil, peanut oil, rapeseed oil, almond oil, palm oil, coconut oil, palm kernel oil, and mixtures thereof at a level that does not impair the formation of the clusters of microcapsules upon dilution of said composition with water and a microcapsule premix, wherein the microcapsule premix comprises a first cationic deposition polymer and a plurality of anionic microcapsules
    wherein the Zeta potential of said microcapsules is less than negative 0.5 millivolts and the weight ratio of said microcapsules to cationic polymer is from about 5:1 to about 12:1; and
    combining the benefit phase with a structured cleansing phase comprising from about 2% to about 50%, by weight of the personal care composition, of an anionic surfactant.

2. The method of making the personal care composition of claim 1, wherein the structured cleansing phase and the benefit phase are in physical contact with each other.

3. The method of making the personal care composition of claim 1, wherein the anionic surfactant is selected from the group consisting of ammonium lauryl sulfate, ammonium laureth sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, potassium lauryl sulfate, and combinations thereof.

4. The method of making the personal care composition of claim 1, wherein the structured cleansing phase further comprises a second cationic deposition polymer.

5. The method of making the personal care composition of claim 1, wherein the anionic surfactant comprises sodium laureth(n) sulfate.

6. The method of making the personal care composition of claim 1, wherein the microcapsules comprise a core material and a wall material, the wall material comprising those formed from melamine-formaldehyde or urea-formaldehyde condensates, melamine-resorcinol or urea-resorcinol condensates, aminoplasts, gelatin, polyurethane, polyamide, polyolefin, polysaccharide, protein, silicone, lipid, modified cellulose, gums, polyacrylate, polyphosphate, polystyrene, polyesters, or a combination thereof.

7. The method of making the personal care composition of claim 1, wherein the first cationic deposition polymer has a molecular weight of 300,000 Da to 2,000,000 Da.

8. The method of making the personal care composition of claim 7, wherein the first cationic deposition polymer comprises polyvinyl formamide.

9. The method of making the personal care composition of claim 8, wherein the anionic microcapsules comprise a shell comprising polyacrylate, melamine formaldehyde, or a combination thereof.

10. The method of making the personal care composition of claim 9, wherein the anionic microcapsules comprise a core comprising perfume.

11. The method of making the personal care composition of claim 10, wherein the weight ratio of the anionic microcapsule to the first cationic deposition polymer is from about 5:1 to about 12:1.

12. The method of making personal care composition of claim 11, wherein the cationic deposition polymer comprises a polyvinyl formamide.

13. The method of making the personal care composition of claim 11, wherein the cationic deposition polymer has a charge density of about 1 meq/g to about 4 meq/g.

14. A method of making a microcapsule-containing personal care composition comprising:
    making a microcapsule premix by combining a first cationic deposition polymer and a plurality of anionic microcapsules
    wherein the Zeta potential of said microcapsules is less than negative 0.5 millivolts and the weight ratio of said microcapsules to cationic polymer is from about 5:1 to about 12:1; and
    combining the premix with a benefit phase comprising at least one triglyceride oil selected from the group consisting of olive oil, sunflower oil, soybean oil, peanut oil, rapeseed oil, almond oil, palm oil, coconut oil, palm kernel oil, and mixtures thereof at a level that does not impair the formation of the clusters of microcapsules upon dilution of said composition with water and a structured cleansing phase comprising from about 2% to about 50%, by weight of the personal care composition, of an anionic surfactant.

15. The method of claim 14, wherein the benefit phase and structured cleansing phase are combined prior to addition of the microcapsule premix.

16. The method of claim 14, wherein the microcapsule premix is added to the benefit phase prior to addition of the cleansing phase.

17. The method of claim 14, wherein the wherein the weight ratio of the anionic microcapsule to the cationic deposition polymer is from about 5:1 to about 12:1.

18. The method of claim 17, wherein the cationic deposition polymer comprises cationic deposition polymer comprises polyvinyl formamide, starch, guar, cellulose, or a combination thereof.

* * * * *